United States Patent
Kosierkiewicz

(10) Patent No.: US 12,004,861 B2
(45) Date of Patent: *Jun. 11, 2024

(54) SYSTEM AND METHOD TO ANALYZE WAVEFORMS FOR ELECTROMYOGRAPHY TESTING

(71) Applicant: Tomasz Andrzej Kosierkiewicz, Mount Vernon, IL (US)

(72) Inventor: Tomasz Andrzej Kosierkiewicz, Mount Vernon, IL (US)

(*) Notice: Subject to any disclaimer, the term of this patent is extended or adjusted under 35 U.S.C. 154(b) by 225 days.

This patent is subject to a terminal disclaimer.

(21) Appl. No.: 17/381,020

(22) Filed: Jul. 20, 2021

(65) Prior Publication Data

US 2021/0345931 A1    Nov. 11, 2021

Related U.S. Application Data

(63) Continuation of application No. 15/956,693, filed on Apr. 18, 2018, now Pat. No. 11,064,931, which is a continuation-in-part of application No. 14/604,715, filed on Jan. 24, 2015, now Pat. No. 9,962,096.

(60) Provisional application No. 61/931,591, filed on Jan. 25, 2014.

(51) Int. Cl.
| | | |
|---|---|---|
| A61B 5/316 | (2021.01) | |
| A61B 5/00 | (2006.01) | |
| A61B 5/11 | (2006.01) | |
| A61B 5/296 | (2021.01) | |
| A61B 5/389 | (2021.01) | |
| A61B 7/00 | (2006.01) | |

(52) U.S. Cl.
CPC .......... *A61B 5/316* (2021.01); *A61B 5/296* (2021.01); *A61B 5/389* (2021.01); *A61B 5/7264* (2013.01); *A61B 5/1104* (2013.01); *A61B 5/4519* (2013.01); *A61B 5/7257* (2013.01); *A61B 5/7415* (2013.01); *A61B 5/7445* (2013.01); *A61B 7/006* (2013.01)

(58) Field of Classification Search
CPC ....... A61B 5/1104; A61B 5/296; A61B 5/316; A61B 5/389; A61B 5/4519; A61B 5/7264; A61B 5/7445; A61B 5/395; A61B 5/397

See application file for complete search history.

(56) References Cited

U.S. PATENT DOCUMENTS

| | | | |
|---|---|---|---|
| 9,962,096 B1* | 5/2018 | Kosierkiewicz | A61B 5/389 |
| 11,064,931 B2* | 7/2021 | Kosierkiewicz | A61B 5/296 |
| 2016/0151626 A1* | 6/2016 | Gorman | A61B 5/395 |
| | | | 607/48 |

* cited by examiner

*Primary Examiner* — Devin B Henson
(74) *Attorney, Agent, or Firm* — Jessica Smith; LOZA & LOZA, LLP

(57) ABSTRACT

A device includes an EMG processing application operable with a processing module to receive an output signal from EMG testing, wherein the output signal represents electrical activity of at least one muscle. The EMG processing application is operable to process the output signal to detect at least one type of waveform of a plurality of types of waveforms from the output signal and display the detected at least one type of waveform.

9 Claims, 8 Drawing Sheets

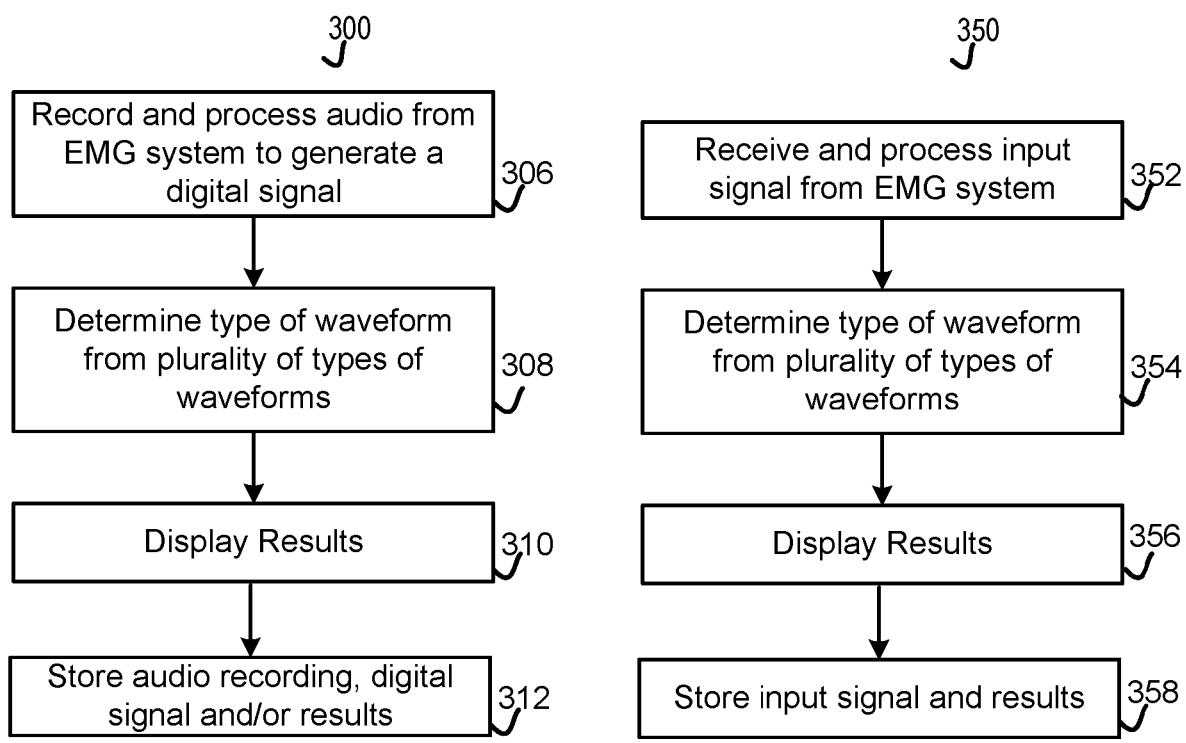

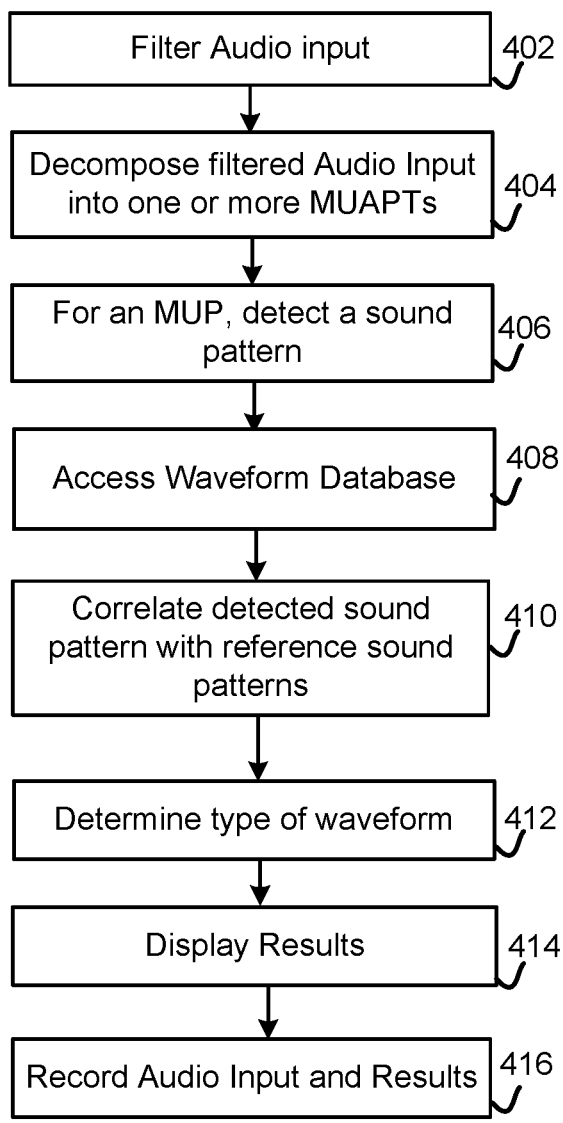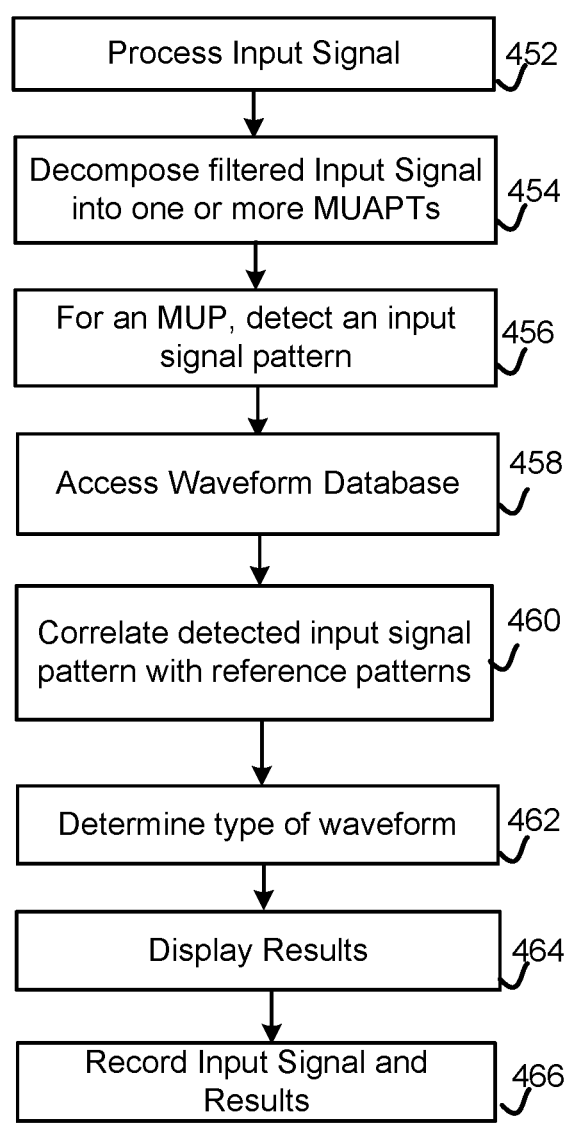
FIG. 7A                    FIG. 7B

SYSTEM AND METHOD TO ANALYZE WAVEFORMS FOR ELECTROMYOGRAPHY TESTING

CROSS-REFERENCE TO RELATED PATENTS

The present U.S. Utility Patent Application claims priority pursuant to 35 U.S.C. § 120 as a continuation application to U.S. patent application Ser. No. 15/956,693, entitled, "SYSTEM AND METHOD TO ANALYZE WAVEFORMS FOR ELECTROMYOGRAPHY TESTING," filed Apr. 18, 2018 and issuing on Jul. 20, 2021 as U.S. Pat. No. 11/064,931, which is incorporated by reference herein and made part of the present U.S. Utility Patent Application for all purposes.

The co-pending U.S. Utility patent application Ser. No. 15/956,693 claims priority pursuant to 35 U.S.C. § 120 as a continuation in part application to prior U.S. patent application Ser. No. 14/604,715, entitled, "SYSTEM AND METHOD TO ANALYZE WAVEFORMS FOR ELECTROMYOGRAPHY TESTING," filed Jan. 24, 2015, and issued on May 8, 2018 as U.S. Pat. No. 9,962,096 which is incorporated by reference herein and made part of the present U.S. Utility Patent Application for all purposes.

The prior U.S. Utility patent application Ser. No. 14/604,715 claims priority pursuant to 35 U.S.C. § 119(e) to U.S. Provisional Application Ser. No. 61/931,591, entitled, "SYSTEM AND METHOD TO ANALYZE WAVEFORMS FOR ELECTROMYOGRAPHY TESTING," filed Jan. 25, 2014, now expired, which is incorporated by reference herein and made part of the present U.S. Utility Patent Application for all purposes.

BACKGROUND

Technical Field

This disclosure relates generally to medical devices and more particularly, but not exclusively, to systems and methods for electromyography testing.

Description of Related Art

The statements in this section provide a description of related art and are not admissions of prior art. An examiner, such as a physician, neurologist, or physiatrist, performs nerve conduction studies on patients. A complementary part of nerve conduction studies is electromyography (EMG). EMG results can reveal nerve dysfunction, muscle dysfunction or problems with nerve-to-muscle signal transmission. EMG testing includes a technique for detecting electrical activity produced by skeletal muscles. Motor neurons transmit electrical signals that cause muscles to contract. In one type of EMG testing, a needle electrode is inserted directly into a muscle and detects the electrical activity in that muscle. Electrical activity of the muscle is sensed by the electrode. An EMG translates these signals into graphs of waveforms displayed on a monitor. In addition, an audio-amplifier is used so the activity can be heard. The examiner may listen to the audio representation and/or view the waveforms on the monitor to evaluate the electrical activity of the muscle as normal or abnormal. The interpretation of an EMG test is thus very subjective due to the evaluation of the waveforms by the examiner.

As such, a need exists to improve EMG testing and in particular to provide a more objective analysis of the waveforms produced by the EMG testing. The potential for computers to analyze the signal/waveforms is within the scope of the present application.

SUMMARY

In an embodiment, a device includes a display; a memory; and an interface configured to receive an output signal of a needle electromyography (EMG) device, wherein a needle electrode is inserted into at least one muscle and records electrical activity of at least one muscle fiber in the at least one muscle and wherein the output signal represents one or more waveforms of the electrical activity of the at least one muscle fiber in the at least one muscle. The device further includes at least one processing device and an EMG processing application stored in the memory and operable with the processing device to: process the output signal; compare the processed output signal to a plurality of output patterns; detect at least one pattern of the plurality of output patterns using the processed output signal; access a waveform database that includes the plurality of output patterns and associated waveform types of electrical activity of muscle fibers, wherein the associated waveform types of the electrical activity of the muscle fibers include one or more of: insertional activity waveform, spontaneous activity waveform, volitional activity waveform or recruitment waveform; identify at least one type of waveform of the plurality of types of waveforms associated with the detected at least one pattern; and display the identified at least one type of waveform on the display.

In an embodiment, the at least one processing device is further operable to diagnose at least one condition based on the identified at least one type of waveform.

In an embodiment, the memory includes a waveform database that includes the plurality of output patterns and the associated waveform types of electrical activity of muscle fibers, wherein the associated waveform types of electrical activity of muscle fibers include one or more of: Normal insertion, Increased insertion, Fasciculations, Fibrillations, or Positive waves.

In an embodiment, the processing device is further operable to: quantify a number of motor units generating the output signal; and determine a count of repetitions for one or more of the motor units during a portion of the output signal.

In an embodiment, the memory includes a patient database for storing the output signal and the identified at least one type of waveform.

In an embodiment, a method includes receiving an output signal of a needle EMG device, wherein the output signal represents electrical activity of at least one muscle fiber; processing the output signal; identifying a first waveform type in the output signal of the electrical activity of the at least one muscle fiber; identifying a second waveform type in the output signal of the electrical activity of the at least one muscle fiber; and displaying a first name of the first waveform type and a second name of the second waveform type and a number of each of the first waveform types and the second waveform types on a display, wherein the first waveform type and the second waveform type of the electrical activity of the at least one muscle fiber includes two or more of: insertional waveform, spontaneous activity waveform, volitional activity waveform or recruitment waveform.

In an embodiment, the method further includes diagnosing at least one condition based on at least one of the first waveform type or the second waveform type.

In an embodiment, the method further includes storing a plurality of reference output patterns and associated waveform types in a waveform database.

In an embodiment, the method further includes detecting an output pattern in the output signal of the needle EMG device; accessing the waveform database; correlating the detected output pattern in the output signal with one of the plurality of reference output patterns stored in the waveform database; and identifying the associated waveform type in the waveform database with the correlated reference output pattern.

In an embodiment, the method further includes quantifying a number of motor units generating the output signal and determining a count of repetitions for one or more of the motor units during a portion of the needle EMG output.

In an embodiment, the method further includes storing a patient database, wherein the patient database includes the output signal of the needle EMG and a name of the first waveform type and a name of the second waveform type and a number of each of the first waveform type and the second waveform type.

BRIEF DESCRIPTION OF THE SEVERAL VIEWS OF THE DRAWINGS

Some embodiments of apparatus and/or methods in accordance with embodiments of the disclosure are now described, by way of example only, and with reference to the accompanying drawings, in which:

FIG. 6A illustrates a logical flow diagram of an embodiment of a method for analyzing EMG testing results from audio;

FIG. 6B illustrates a logical flow diagram of an embodiment of a method for analyzing EMG testing results from an input signal;

FIG. 7A illustrates a logical flow diagram of an embodiment of another method for analyzing EMG testing results from audio;

FIG. 7B illustrates a logical flow diagram of an embodiment of another method for analyzing EMG testing results from an input signal;

DETAILED DESCRIPTION

Figure 1:
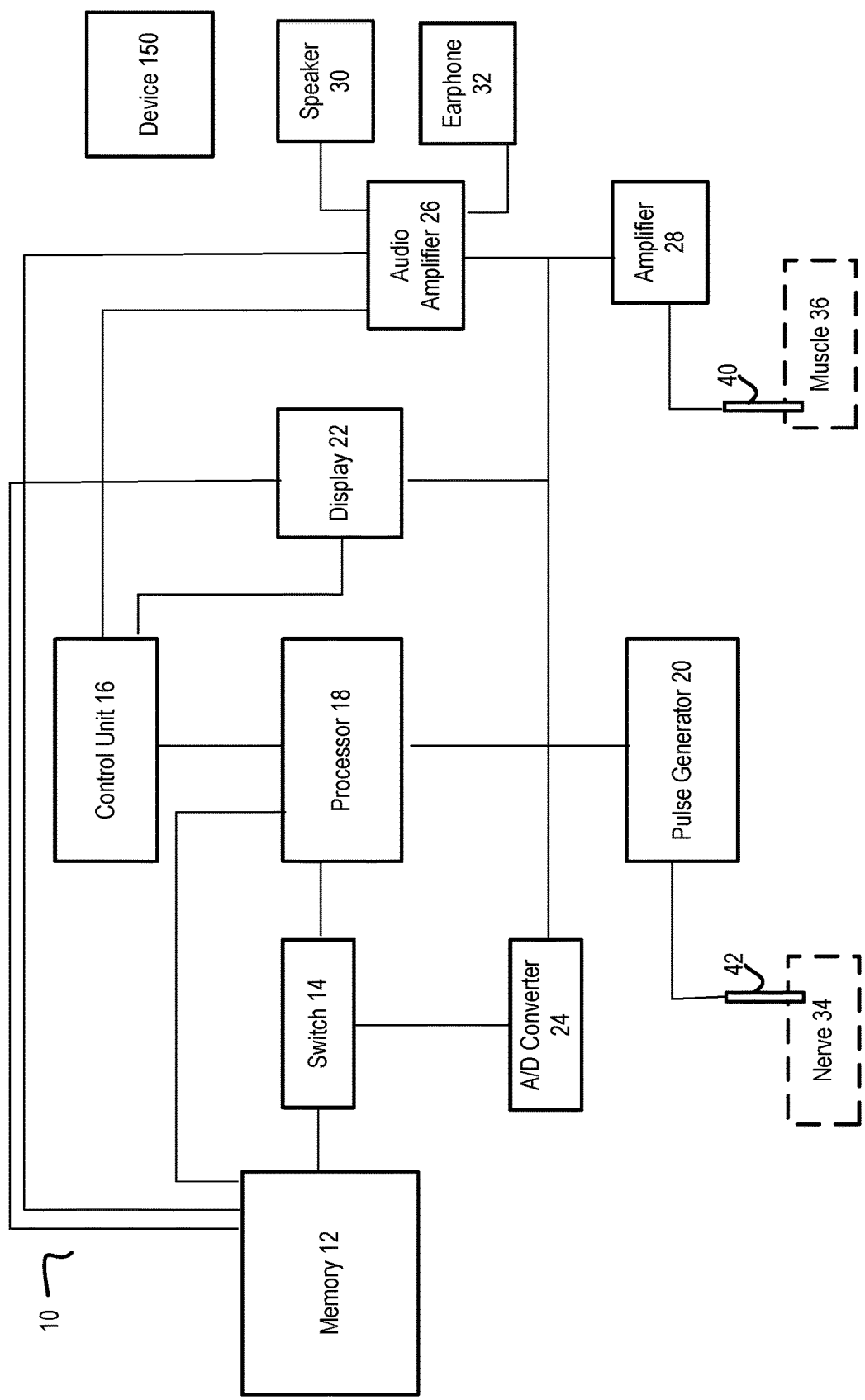
FIG. 1 illustrates a schematic block diagram of an embodiment of a system for performing EMG testing.

The description and drawings merely illustrate the principles of various embodiments. It will thus be appreciated that those skilled in the art will be able to devise various arrangements that, although not explicitly described or shown herein, embody the principles herein and in the claims and fall within the spirit and scope of the disclosure. Furthermore, all examples recited herein are principally intended expressly to be only for pedagogical purposes to aid the reader in understanding the principles of the embodiments and the concepts contributed by the inventor to furthering the art, and are to be construed as being without limitation to such specifically recited examples and conditions. Moreover, all statements herein reciting principles, aspects, and embodiments, as well as specific examples thereof, are intended to encompass equivalents thereof.

An embodiment may include a data acquisition system including an analog to digital converter, a computer processor and a waveform memory in which is stored digital data from an analog to digital (A/D) converter corresponding to an input signal. A processor provides a trigger responsive to a characteristic of a frequency component or any components of the input signal to cause a memory to save waveform data in a memory. A frequency characteristic may be determined, for example, by carrying out a synchronized recursive discrete Fourier transform which is updated for the selected frequency component or components with each new sample from the A/D converter.

As explained in U.S. Pat. No. 4,816,813A, a waveform segment constituting several points of digitized waveform data from a digitizer is stored in a pixel memory which has a number of memory locations corresponding to the number of pixels in the horizontal screen width of a raster scan video screen. As each new data point is written into a sequentially higher location in the memory, the data at the memory location that is a selected number of memory locations lower, constituting the desired number of pixels in the waveform segment, is erased. When a full new segment of data is in the waveform memory, the contents of the memory is provided to a raster scan graphics control unit which causes a new raster scan frame to be written on the video monitor screen. Only the portion of the waveform corresponding to the segment of waveform data in the waveform memory is illuminated on the screen. New data continues to be written into the waveform memory until another full segment of waveform data is in the memory and all previous waveform data points have been erased. The content of the waveform memory then is again provided to the raster scan graphics control which causes another raster scanned frame to appear on the video monitor screen, with the new segment of waveform illuminated on the video screen displaced sequentially from the previously displayed waveform segment.

In an embodiment described herein, once any audio is generated during the needle EMG exam, the EMG Processing Application 154 should start producing output in a form of written types of waveforms which may be displayed on the display and/or may be recorded in the memory 12 and/or memory 60 of the device 150. Alternatively, the input could be recorded and processed remotely, as describe in U.S. Pat. No. 8,972,263, which is hereby incorporated by reference herein.

An input signal represents an electrical signal (activity) generated by a muscle and detected, e.g., by a needle electrode inserted into the muscle. An event represents a type of a waveform (EMG activity) to be recognized by a device as described herein.

FIG. 1 illustrates a system 10 for stimulating and recording responses from a muscle 36 which may be a human muscle or other living organism. The system 10 includes a stimulating device 42 which may be an electrode/needle. The stimulating device 42 may be used to stimulate a nerve 34 that then may activate the muscle 36. A measuring device 40 includes another electrode/needle to record response signals from the muscle 36 during the stimulation of the nerve 34. In another embodiment, the nerve 34 may not be stimulated. The measuring device 40 may be connected to an amplifier 28 which may amplify the signals from the muscle 36 during normal activity without stimulation.

The amplifier 28 may be connected to an A/D converter 24 to convert the analog signal from the amplifier 28 to a digital signal and may be connected to an audio amplifier 26 to amplify the signal from the amplifier 28 to a sufficient level in order to be heard by an evaluating individual. The audio amplifier 26 may be connected to a speaker 30 and/or an earphone 32. The control unit 16 may be connected to the audio amplifier 26 to control the operation (such as volume and on/off) of the audio amplifier 26, and the control unit 16 may be connected to other user interface devices such as a keyboard, mouse, etc.

audio signals from the speaker 30 and buttons 56a-d in order to control the device 150. The device 150 may determine the type of waveform for example by the type of muscle being examined and from the audio emitted from the speaker 30. The screen may be pressure/touch sensitive in order to respond to pressure such as tapping in order to select and control the device 150 instead or in addition to using buttons 56a-d.

The device 150 is operable to not only recognize the type of waveform as a predetermined sound pattern from the muscle 36, but also could quantify it for the given muscle 36, and if needed, populate appropriate tables for example as the table shown below and store the table within the memory 60 of the device 150 or the memory 12.

TABLE 1

| | | Insertional | | | | Volitional Activity | | | | Recruitment | | |
|---|---|---|---|---|---|---|---|---|---|---|---|---|
| | | Activity | Spontaneous Activity | | | MUP | MUP | MUP | MUP | Max | Max | |
| | | Insertional | Fibs | +Wave | Fasics | Poly | Amp | Dur | Config | Pattern | Amp | Pattern | MaxEffort |
| Gastrocnemius Medial Head | R | Normal | None | None | Few | None | Decr | Decr | Poly | Norm | Sl Decr | Reduced | Max |
| Tibialis Anterior | R | Increased | None | 1+ | None | None | Norm | Norm | Poly | Norm | Sl Decr | Reduced | Max |
| Vastus Lateralis | R | Normal | None | None | None | None | Norm | Norm | Poly | Norm | Norm | Reduced | Max |
| Vastus Medialis | R | Normal | None | None | None | None | Norm | Norm | Norm | Norm | Sl Decr | Reduced | Max |

The output of the amplifier 28 may be connected to a display device 22 which may display the signal obtained from the muscle 36, and the output of the amplifier 28 may be connected to an A/D converter 24 to convert the analog signal from the muscle 36 to a digital signal. The digital signal is transmitted to a switch 14 which may be controlled and connected to the processor 18 which may be connected and controlled by the control unit 16. The processor 18 may open the switch 14 to allow the digital signal to be stored in the pixel/waveform memory 12, or alternatively, the processor 18 may close the switch 14 to prevent the storage of the digital signal in the memory 12. The processor 18 may control the memory 12 to activate the transmission of the stored digital signals from the memory 12 to the display 22 and/or to the audio amplifier 26.

In operation, the pulse generator 20 activates the stimulating device 42 to transmit one or more stimulating pulses from the pulse generator 20 to the nerve 34 which activates the muscle 36. The response signal from the muscle 36 is transmitted to the device 150 and the amplifier 28.

During the needle EMG exam, the electrical signal from the muscle 36 is transmitted to the device 150 and the amplifier 28. The analog signal is transmitted to the audio amplifier 26 and transmitted to the speaker 30 and the earphone 32 so that the user can listen to the signal generated by the muscle 36. In addition the analog signal may be converted to a digital signal and may be selectively stored in the memory 12 under the control of the control unit 16 through the processor 18. A device 150 may be positioned sufficiently close to the speaker 30 in order to detect the audio from the audio amplifier 26.

Figure 2:
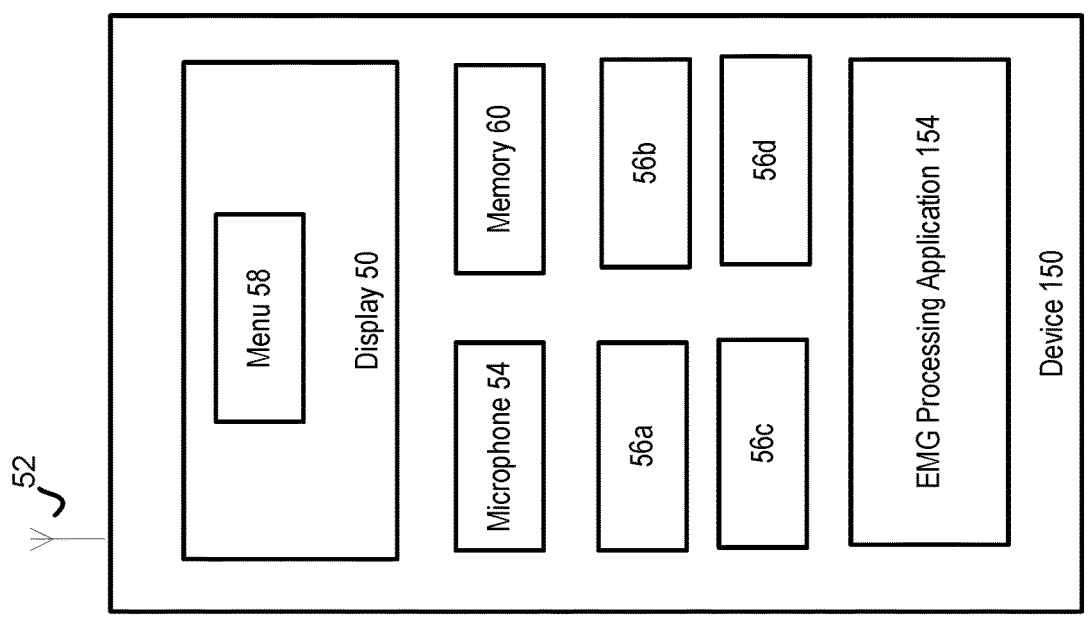
FIG. 2 illustrates a schematic block diagram of an embodiment of a device for analyzing EMG testing results.

FIG. 2 illustrates a schematic block diagram of an embodiment of device 150. The device 150 may be wirelessly or wired connected to the processor 18. The device 150 may include an antenna 52 to communicate with the processor 18, a display 52 to display information for the user of the device 150, a microphone 54 in order to receive the As seen in Table 1, the associated waveform types of the electrical activity of the muscle fibers include one or more of: insertional activity waveform, spontaneous activity waveform, volitional activity waveform or recruitment waveform.

The device 150 may include an EMG processing application 154. The EMG processing application 154 recognizes sound patterns in the audio input signal and is operable to recognize one or more types of waveform as a predetermined sound pattern in the audio input signal. In an embodiment, the EMG processing application 154 may include similar processing techniques as in speech recognition software, wherein the spoken word is the audio input and the written word is the output (what is on the display 50).

In the EMG processing application 154 of the device 150, the audio generated in response to the muscle 36 activity is input to the microphone 54 of the device 150. The EMG processing application 154 will recognize a sound pattern in the audio that is associated with a particular waveform, and the written type (name) of the waveform will be the output and displayed on the display 50 and may be transmitted to the processor 18 and stored within the memory 12.

During use, the user places the device 150 next to the audio source (speaker) 30 of the EMG equipment, tap or select the start tab or button, choose the muscle group, the specific muscle from a menu 58 from the display 135, and thus start the recording of the audio signal from the muscle 36 (waveform recognition). Alternatively, tapping or selecting the "Default Settings" of the device 150 would do the same. Once any audio is generated during the needle EMG exam, the EMG processing application 154 should start producing output in a form of written types of waveforms which may be displayed on the display 50 and/or may be recorded in the memory 12 and/or memory 60 of the device 150. Alternatively, the input could be recorded locally and then processed remotely. See, for example, U.S. Pat. No. 8,972,263, which is incorporated by reference herein, that describes a system operable to perform local voice recognition and remote voice recognition.

The input data (the output signal/electrical activity/sound) of a fibrillation potential produces a name (event) "fibrillation potential" on the screen 50 of the device 150. The input data (the output signal/electrical activity/sound) of positive sharp wave will produce the event "positive sharp wave" or abbreviation "PSW" on the screen. A list of waveform types may include one or more of: Polyphasic units, Normal insertion, Increased insertion, End-plate noise, End-plate spike, Fasciculation, Fibrillations, Positive waves, Complex repetitive discharges (CRD), Myotonic discharges, Myokymic discharges, Neuromyotonic charges, and their subsets, but not limited thereto. Waveforms from the muscle 129 may be a short waveform with a maximum for a longer duration of up to 20 ms. (Although a few types of waveforms can run in trains).

Embodiments herein provides for quantifying the events and populating tables with waveform data such as Table 1. Furthermore, embodiments herein may export the waveform data to an appropriate report generator program. Embodiments provide for the ability of when examining a particular muscle, having choice of selecting the desired muscle from the menu, and may not allow the operator to move on to a second muscle unless adequate motor unit sampling has been completed for the first muscle and the number of needle passes is considered satisfactory. Embodiments may be adapted to distinguish non-speech audio input events (the desired EMG sound pattern events) from speech or other audio input (non-desired events).

The EMG Processing Application 154 may be adapted to synthesize reference pattern data from stored audio reference pattern data in a memory 60 of the device or memory 12 and patterns similar to stored reference pattern data. For example, correlations or other calculations may be performed to determine the differences between data representing the reference pattern and data representing the input. The reference pattern data with the correlations having the least differences may then be determined. For the review process, the EMG Processing Application 154 may be adapted to allow: recorded input/sound review or time based events (recognized EMG sounds) or both. For example, the input/sound of fibrillation potential will produce a name of an event, such as "fibrillation potential" on the display 50. The input/sound of a positive sharp wave will produce the name positive sharp wave or abbreviation PSW (event) on the display 50. In addition, recorded input/sound may be synchronized with time based events (i+ii) where i is recorded input/sound review only, and ii is time based event review only (recognized EMG inputs/sounds).

Figure 3:
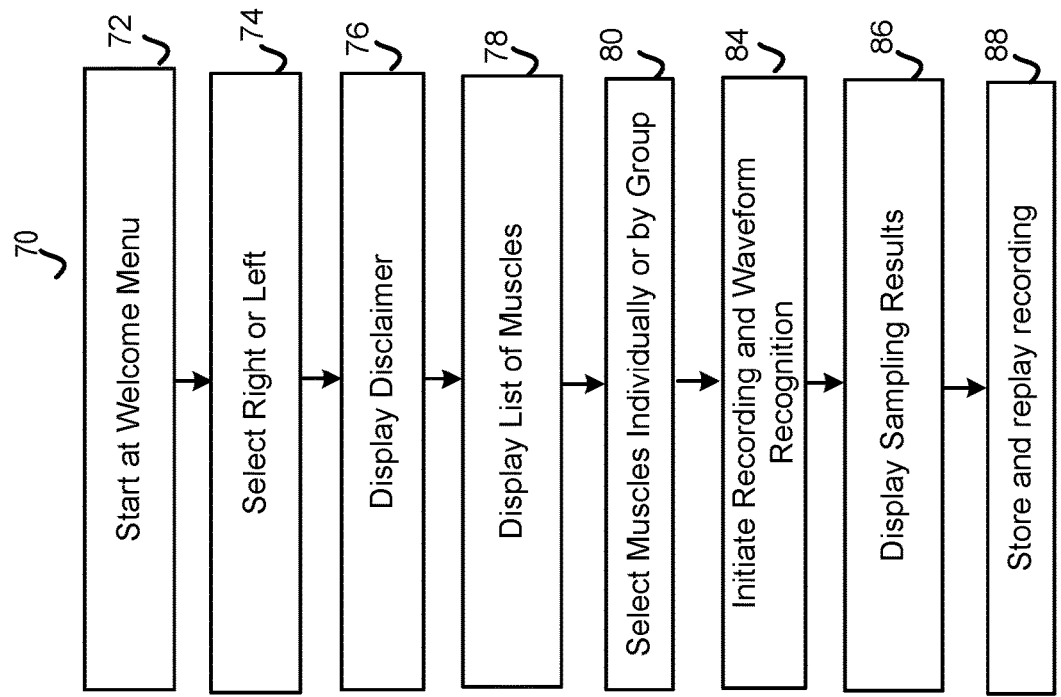
FIG. 3 illustrates a logic flow diagram of an embodiment of a method for analyzing EMG testing results.

FIG. 3 illustrates a logic flow diagram of an embodiment of a method 70 for performing waveform recognition by the device 150. In step 72, device 50 displays a welcome screen with tabs or buttons for selecting, "START RIGHT" "START LEFT" "REVIEW AUDIO" "REVIEW EVENTS" "REVIEW ALL". In step 74, device 50 receives a selection of "START RIGHT" or "START LEFT". In step 76, the device 50 displays a disclaimer with an option "Do not show it again". In step 78, the device 50 displays a list of the muscles. The list of the muscles can be scrolled down starting with "default settings". Alternatively muscles may be grouped. In that case the second (next screen) would have the tabs of the groups of the muscles, again starting with "Default settings". Tapping on the tab of a group of muscles would open the next screen—list (tabs) of individual muscles within the given group. Once a muscle to be examined is selected by tapping the appropriate tab in step 80, the device displays a new screen and recording and waveform recognition is initiated in step 84. Events can be recognized and listed with the time of occurrence and the number of occurrences can be added up and displayed as a sum.

Insertional activity (initial needle passes) in step 86 can be added up as well, and the sampling can be labeled as satisfactory if sufficient number of needle passes has been detected. Then, once the screen is closed (by tapping on the screen) it reverses back to the prior screen—the list (tabs) of individual muscles within the given group—the background of the tab with the name of the examined muscle will turn green. Red background shows inadequate sampling. For example, once the testing is finished the screen with the list of all muscles shows the examined muscle tabs as either green, indicating adequate sampling or as red, indicating inadequate sampling. Adequate sampling may also be signaled to a specific signal (sound). A recording of an already completed muscle may also be selected from a menu on the display for review. Recording can be displayed continuously with recognized time based events synchronized with the sound recording in step 88.

Alternatively, a list of time based events or only the input/sound recording can be reviewed separately. In another embodiment the recording can be continuous (in default settings without the need to select individual muscles) again. A recording can be displayed continuously with recognized events synchronized with the sound recording. Alternatively, a list of time based events or only the input/sound recording can be reviewed separately.

In an embodiment at least twelve (12) events of IA (insertional activity, both normal and/or increased) are needed per muscle examined for an adequate muscle sampling. Between each muscle examined there is a pause (when needle is removed from one muscle and inserted into another muscle during the EMG procedure). The pause (certain length of time) will trigger the summation process of IAs as well as other events. In either case, the entire recording can be scrolled back and forth. At the end of the exam, the entire file can be saved within the memory 60 of the device 150 or memory 12 of device 150. The data is saved and exported to the appropriate report generator program in step 88.

Figure 4:
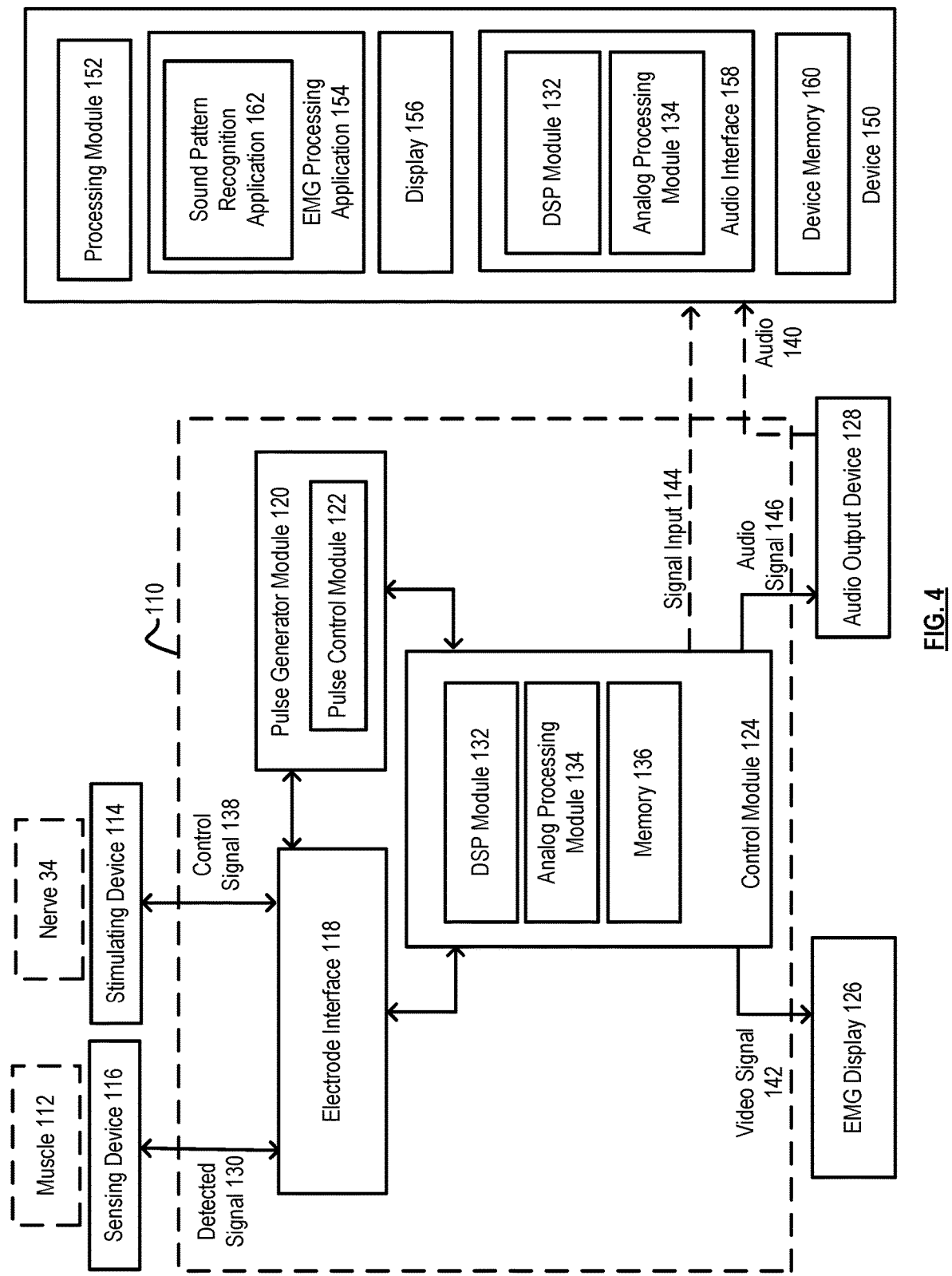
FIG. 4 illustrates a schematic block diagram of another embodiment of a system for performing EMG testing.

FIG. 4 illustrates a schematic block diagram of another embodiment of an EMG system 110 for performing EMG testing. In an embodiment, the EMG system 110 is operable to activate a muscle 112 and record electrical activity responses from the muscle 112. The EMG system 110 detects the electrical potential generated by muscle cells when these cells are electrically or neurologically activated. In an embodiment, the muscle 112 is a human muscle but may also be a non-human muscle such as from an animal. The EMG system 110 includes a stimulating device 114, such as an electrode or needle, for stimulating nerves 34 that activate the muscle 112. The EMG system 100 also includes a sensing device 116, such as another electrode or needle, for recording the electrical activity from the muscle 112 in response to the stimulation of the nerve. Generally, the sensing device 116 includes EMG electrodes placed on the surface of the skin overlying the muscles being evaluated, or needle electrodes which penetrate the tissue being studied. In addition to these active electrodes, a ground reference electrode is generally also applied to the patient.

An electrode interface 118 is operably coupled to the stimulating device 114 and sensing device 116 and to pulse generator module 120. The pulse generator module 120 includes a pulse control module 122 that communicates with the stimulating device 114, sensing device 116 and control module 124. The pulse generator module 120 receives commands from the control module 124, such as registration information, transmission frequency commands, amplifier gain commands, transmitter control commands, power saving mode, etc. The pulse generator module 120 processes these commands and responsively configures the stimulating devices 114 and sensing devices 116 accordingly.

In another embodiment, during EMG testing, the muscle 12 may not be stimulated by stimulating device 114. Instead, the sensing device 116 senses electrical activity during normal motion of the muscle 112 or volitional activation.

The detected signal 130 from the sensing devices 116 is generally weak and typically measured in microvolts. As such, the electrical interface 118 amplifies the detected signal 130 sensed from the muscle 112. Alternatively, the electrical interface 118 transmits the detected signal 130 to the control module 114 that amplifies and processes the detected signal 130. For example, control module 114 includes a digital signal processing (DSP) module 134 and analog processing module 134 that process the detected signal 130. For example, the analog processing module 134 may include a preamplifier followed by one or more additional stages of amplification that boost the detected signal to a usable level as well as filters that minimize the effects of interference arising from sources other than the muscles being studied.

In an embodiment, the DSP module 132 includes an A/D converter that converts the amplified detected signal to a digital signal for further processing. For example, the DSP module 132 may perform rectification of the amplified signal to a single polarity frequency (usually positive). The purpose of rectifying a signal is to ensure the raw signal does not average zero, due to the signal having positive and negative components. The DSP module 132 may analyze the signal and calculate a mean, integration and fast Fourier transform (FFT) of the signal. The DSP module 132 and analog processing module 134 may be one module or split into multiple modules with different inputs and outputs.

In an embodiment, the control module 124 further includes a memory 136 to store the received detected signal 130 and processed signals, such as the video signal 142 and audio signal 146. The audio signal 146 is transmitted to an audio output device 128, such as a speaker or earphones. The audio output device 128 generates audio 140 that may be heard by the operator. The video signal 142 is transmitted to an EMG display 126, such as a computer monitor, TV screen or other type of display. The control module 124 may also generate a signal input 144 that includes the audio signal 146 and/or video signal 142 or other representation of the detected signal 130. The signal input 144 may be transmitted to the user device 150 wirelessly using a wireless transceiver. For example, the wireless transceiver 110 may operate in a Bluetooth protocol (such as a Bluetooth Low Energy Transmitter (BLE 4.2)), wireless local area network protocol such as IEEE 802.11a, g, n, ac, etc. or may utilize a standard protocol in the 900 MHz range, such as IEEE 802.11ah, Zigbee, etc., or through a short range radio frequency (RFID) protocol, cellular protocol, or other short range or long range wireless communication protocol. In addition or alternatively, the signal input 144 may be transmitted to the user device 150 via a wired connection, e.g. using a LAN or WAN protocol.

In operation, the sensing device 116 detects the electrical activity from the muscle 36 and generates the detected signal 130. The detected signal 130 is transmitted to the analog processing module 134 and/or DSP module 132 to generate the video signal 142 and the audio signal 146. The audio signal 146 is transmitted to the audio output device 128, such as a speaker or earphone, so that the examiner can listen to the audio 140. In addition the detected output signal 130, the output audio signal 146 and/or the output video signal 142 are selectively stored in memory 136 by the control module 124.

A motor unit is defined as one motor neuron and the muscle fibers that it innervates. When a motor unit fires, the impulse (called an action potential) is carried down the motor neuron to the muscle. The area where the nerve contacts the muscle is called the neuromuscular junction, or the motor end plate. After the action potential is transmitted across the neuromuscular junction, an action potential is elicited in all of the innervated muscle fibers of that particular motor unit. The sum of all this electrical activity is known as a motor unit action potential (MUP). This electrophysiologic activity from multiple motor units is the detected signal 130 typically evaluated during EMG testing. The composition of the motor unit, the number of muscle fibers per motor unit, the metabolic type of muscle fibers and many other factors affect the shape of the motor unit potentials (MUPs). EMG signals are essentially made up of superimposed motor unit action potentials (MUPs) from several motor units.

For a thorough analysis, the measured EMG signals can be decomposed into their constituent MUPs. MUPs from different motor units tend to have different characteristic shapes, while MUPs recorded by the same electrode from the same motor unit are typically similar. Notably MUP size and shape depend on where the electrode is located with respect to the fibers and so can appear to be different if the electrode moves position. The electrical source is the muscle membrane potential of about −90 mV. Measured EMG potentials range between less than 50 μV and up to 20 to 30 mV, depending on the muscle under observation.

Typical repetition rate of muscle motor unit firing is about 7-20 Hz, depending on the size of the muscle (eye muscles versus seat (gluteal) muscles), previous axonal damage and other factors. Damage to motor units can be expected at ranges between 450 and 780 mV. A variety of different MUP waveforms are generated in normal and diseased muscles.

Currently, an automated machine cannot recognize the various types of MUP waveforms or distinguish a number of MUP waveforms. Clinical EMG testing therefore relies not only on an electromyographer's ability to recognize individual MUP waveforms occurring alone, but also occurring in combination with other MUP waveforms. Currently, an electromyographer must learn to recognize these MUP waveforms empirically by visually recognizing the MUP waveforms on the EMG display 126 or by hearing the audio 140 representing the waveforms from the audio output device 128.

In an embodiment, a device 150 is operable to receive and process the audio 140 or the signal input 144 and to determine one or more types of MUP waveforms occurring alone or occurring in combination with other MUP waveforms in the signal input 144 and/or audio 140. The device 150 includes a processing module 52, EMG processing application 154, display 156 and audio interface 158 and device memory 160. In an embodiment, the device 150 is a user device, such as a laptop, smartphone, smart tablet, smart watch, etc. In another embodiment, the device 150 or one or more parts of the device 150, such as EMG processing application 154, is incorporated into the EMG system 110, such as part of the control module 124. The device includes a display 156 that may be a touch screen to select and control the device 150 or the device 150 may also include other user interfaces such as keyboards, mouse, touchpads, etc.

In an embodiment, the device 150 detects the audio 140. For example, the device 150 includes an audio interface 158 such as a microphone that is operable to detect the audio 140 from the audio output device 128 and generate a digital signal for analysis. For example, the audio interface 158 may also include a DSP module 132 and analog processing module 134 that processes the detected audio 140 and generates a digital signal. In another embodiment, the device 150 is operably coupled either wirelessly or wired to the control module 124 or audio output device 128 to receive a digital or analog signal input 144 either wirelessly or via a wired interface from the EMG system 110.

The device 150 is operable to determine a type of waveform from the audio 140 and/or the signal input 144. Different types of waveforms have distinct sound patterns. For example, the device 150 is operable to determine that a waveform is one type of a plurality of types of waveforms from its sound or wave pattern. In an embodiment, the device 150 is also operable to quantify a number of sources of the waveforms in the audio output 140 and/or the signal input 144, e.g. potentials that represent the contraction of individual muscle fibers or a number of motor unit action potential (MUP) waveforms. The device 150 is then operable to record and display the results on display 156. The results are stored within the device memory 160 of the device 150. For example, the results on the display 156 may include a table such as Table 1 above.

The EMG processing application 154 running on the processing module 152 of the device 150 includes a sound or audio pattern recognition application 162. The EMG processing application 154 is operable to process and correlate the input/sound pattern of the audio 140 with a particular type of waveform. For example, the input/sound pattern of the audio 140 is compared with a plurality of stored reference waveform patterns. Correlation or other calculations are performed to determine the stored reference pattern that is most similar or has least differences with the input/sound pattern of the audio 140. The name of the type of the waveform is then output and displayed on the display 156 and may be stored within the device memory 150.

Figure 5:
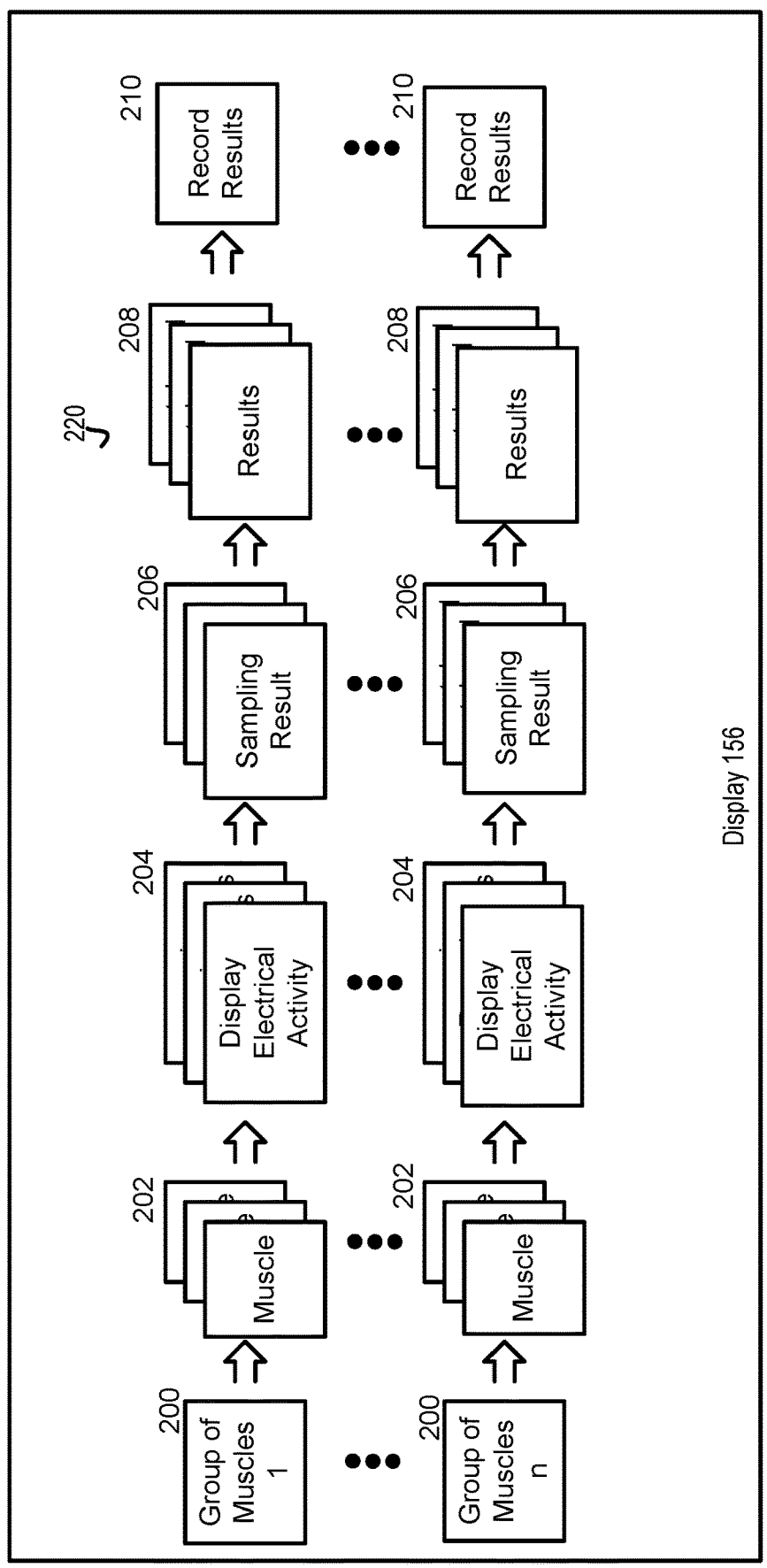
FIG. 5 illustrates a schematic block diagram of an embodiment of a graphical user interface displayed on a device for analyzing EMG testing results.

FIG. 5 illustrates a graphical user interface (GUI) 220 displayed on the display 156 of the device 150. The GUI 220 is only exemplary of the various options and information that may be displayed. The GUI 220 may be separated into a number of different windows or menus or include additional or alternative windows or menus. In an embodiment, the GUI 220 includes an option to select a muscle being tested by the EMG system 110. The GUI 220 displays a plurality of group of muscles 200 for a patient from a drop down menu or window. The GUI 220 then displays a plurality of muscles 202 for the selected group of muscles. One of the plurality of muscles 202 is then selected During EMG testing of the muscle, the device 150 receives the audio 140 using a microphone placed an audible distance from the audio output device 128, such as a speaker, of the EMG system 110. Alternatively, or in addition to the audio 140, the device 150 may receive an analog or digital signal input 144 from the EMG system 110. A user of the device 150 selects a group of muscles 200 and a specific muscle 202 from GUI 220. The examiner may then start recording the audio 140 or the signal input 144 generated in response to the sensing device 116 from the selected muscle 202. When audio 140 is generated during the EMG testing, EMG processing application 154 processes the audio 140.

The GUI 220 may display a sampling result 206, e.g. if sufficient data is collected for the selected muscle, the screen tab may turn green. The device 150 may be configured to not allow an examiner to select a second muscle for testing unless adequate motor unit sampling has been completed for the first muscle and/or sufficient number of needle passes has been detected, e.g. as indicated by a screen/tab turning red.

When sufficient data is received, the EMG processing application 154 determines one or more types of waveforms and/or number of detected waveforms and displays the results 208 in a window or tab on the device display 156. The results may also be recorded in the device memory 136 automatically or by selecting a record results 210 option. This process may be repeated for a plurality of muscles in one group of muscles 200 and/or for a plurality of muscles 202 in different groups of muscles 200.

When EMG testing is complete, a list of muscles 202 shows the sampling result 206 for an examined muscle as either green, meaning adequate sampling, or as red, meaning inadequate sampling. Adequate sampling may also be signaled by a specific signal(sound). Selecting a completed muscle 202 displays the electrical activity recording and thus allows for additional review. Alternatively, a list of time based events for the electrical activity or only the sound recording can be selected and reviewed separately. In another embodiment, the recording may be continuous (in default settings without the need to select individual muscles). The recording can be displayed continuously with recognized events synchronized with the sound recording. Alternatively, between each muscle examined, there is a pause (when needle is removed from one muscle and before it is inserted into another muscle during the EMG procedure). The pause (certain length of time) will trigger the summation process of events for a given muscle. A list of time based events or only the sound recording can be reviewed separately. In either case, the entire recording can be scrolled back and forth. At the end of the EMG testing, the entire file can be saved by the device 150. The data can be saved and exported to the appropriate report generator program.

FIG. 6A illustrates a logical flow diagram of an embodiment of a method 300 for analyzing EMG testing results from the audio 140. The method 300 begins when the device 150 detects audio 140 using a microphone or similar device. The device 150 records the audio 140 and processes the audio 140 from the EMG system 110 in step 306. The device 150 for example converts the audio 140 into a digital signal for processing.

In step 308, the EMG processing application 154 operating with processing module 152 of device 150 processes the digital signal to determine one or more types of waveforms from a plurality of types of waveforms in the audio 140. For example, using pattern recognition techniques, the device 150 determines that the digital signal includes an event, such as a type of waveform named "fibrillation potential". In step 310, device 150 then displays the result, e.g. "Fibrillation potential" on the display 156. The time of occurrence of the event and the number of occurrences can be determined and displayed as well.

For example, the EMG processing application 154 operating with processing module 152 of device 150 determines that the audio 140 includes a positive sharp wave sound pattern and determines that the type of waveform is named "positive sharp wave" and displays this or an abbreviation "PSW" on the display 156. A list of a plurality of type of events or waveforms that may be detected in the audio signal 140 includes, inter alia, Long duration MUP, Short duration MUP, Polyphasic unit, short duration, Polyphasic units long duration, Normal insertion, Increased insertion, Cramp discharge, End-plate noise, End-plate spike, End-plate spike and noise, Fasciculation, Fibrillations, Positive wave, CRD (Complex repetitive discharges), Myotonic discharges, Myokymic discharges, Neuromyotonic charges, and theirs subsets, but not limited to.

In addition, the EMG processing application 154 operating with processing module 152 of device 150 is operable to quantify the number of sources of waveforms or events detected in the audio 140. The results may be used to populate one or more tables, such as Table 1 above, with waveform data for display and storage. Furthermore, the device 150 may export the results to an appropriate report generator program. The recordings of the audio 140 and the digital signal may be stored along with the results in step 312.

FIG. 6B illustrates a logical flow diagram of an embodiment of a method 350 for analyzing EMG testing results from an input signal 144. The method 350 begins when the device 150 receives the input signal 144 either wirelessly or via a wired connection from the EMG system 110. The device 150 stores and processes the input signal 144 from the EMG system 110 in step 352. In step 354, the EMG processing application 154 operating with processing module 152 of device 150 processes the input signal 144 to determine one or more types of waveforms from a plurality of types of waveforms. For example, using pattern recognition techniques, the device 150 determines that the input signal 144 includes an event, such as a type of waveform named "fibrillation potential". In step 356, device 150 then displays the result, e.g. "Fibrillation potential" on the display 156. The time of occurrence of the event and the number of occurrences can be determined and displayed as well. In addition, the EMG processing application 154 operating with processing module 152 of device 150 is operable to quantify the number of sources of waveforms or events detected in the input signal 144. The results may be used to populate one or more tables, such as Table 1 above, with waveform data for display and storage. Furthermore, the device 150 may export the results to an appropriate report generator program. The input signal 144 may be stored along with the results in step 358.

FIG. 7A illustrates a logical flow diagram of another embodiment of a method 400 for analyzing EMG testing results from audio. The method 400 includes detecting the audio 140 using a microphone or other sound detection device and recording the audio 140. The audio 140 is processed in step 402 to filter the desired electrical activity input events (e.g., the desired EMG sound pattern events) from non-desired events, such as speech audio input or noise. In an embodiment, in step 404, the filtered audio is decomposed into one or more source MUAPTs. For example, the filtered audio may include a plurality of individual motor unit action potential trains (MUAPTs). These individual MUAPTs are identified and may be displayed. For each of the MUP waveforms in an MUAPT, the device 150 detects a sound pattern in step 406.

A waveform database is accessed that stores reference sound patterns and names of associated types of waveforms in step 408. A detected sound pattern in the recorded audio is correlated with the reference sound patterns until a match is determined in step 410. The associated type of waveform is thus determined based on the matching reference sound pattern in step 412. The result is displayed in step 414 and recorded in step 416 along with the audio input.

FIG. 7B illustrates a logical flow diagram of another embodiment of a method 450 for analyzing EMG testing results from an input signal 144. The method 400 includes receiving the input signal 140 wirelessly or via a wired interface and storing the input signal 144. The input signal 144 is processed in step 452 to filter the desired electrical activity input events (e.g., the desired EMG pattern events) from non-desired events, e.g., noise. In an embodiment, in step 454, the filtered signal is decomposed into one or more source MUAPTs. For example, the filtered signal may include a plurality of individual motor unit action potential trains (MUAPTs). These individual MUAPTs are identified and may be displayed. For each of the MUP waveforms in an MUAPT, the device 150 detects an input signal pattern in step 456.

A waveform database is accessed that stores reference wave patterns and names of associated types of waveforms in step 458. A detected wave pattern in the filtered signal is correlated with the reference wave patterns until a match is determined in step 460. The associated type of waveform is thus determined based on the matching reference wave pattern in step 462. The result is displayed in step 464 and recorded in step 466.

Figure 8:
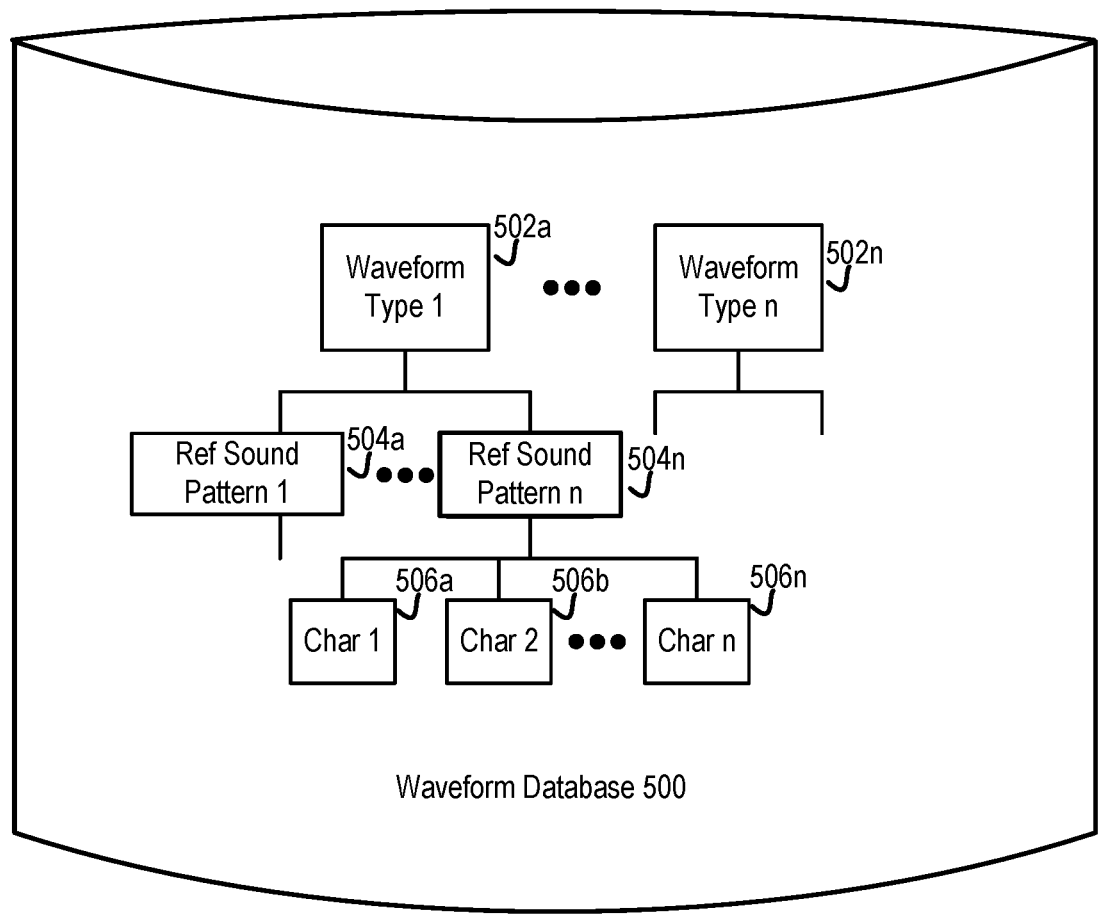
FIG. 8 illustrates a schematic block diagram of an embodiment of a waveform database.

FIG. 8 illustrates a schematic block diagram of an embodiment of a waveform database 500. The waveform database 500 is stored, for example, in device memory 160 or other memory accessible by the EMG processing application 154 or processing module 152 of device 150. The waveform database 500 includes a plurality of waveform types 502 and reference (Ref) sound (e.g., wave) patterns 504. Since a waveform type 502 may have slight variations, one or more reference sound patterns 504 may be associated with a waveform type 502. Various characteristics (Char) 506 may be stored and associated with a reference sound pattern 504. For example, a characteristic 506 may include a typical duration, peak voltage, number of peaks, repetition rate, etc. for the reference sound pattern. The detected sound pattern for a waveform is correlated with one or more reference sound patterns in the waveform database 500 until a match is determined. The type of waveform is thus determined based on the matching reference sound patterns from the waveform database 500.

Figure 9:
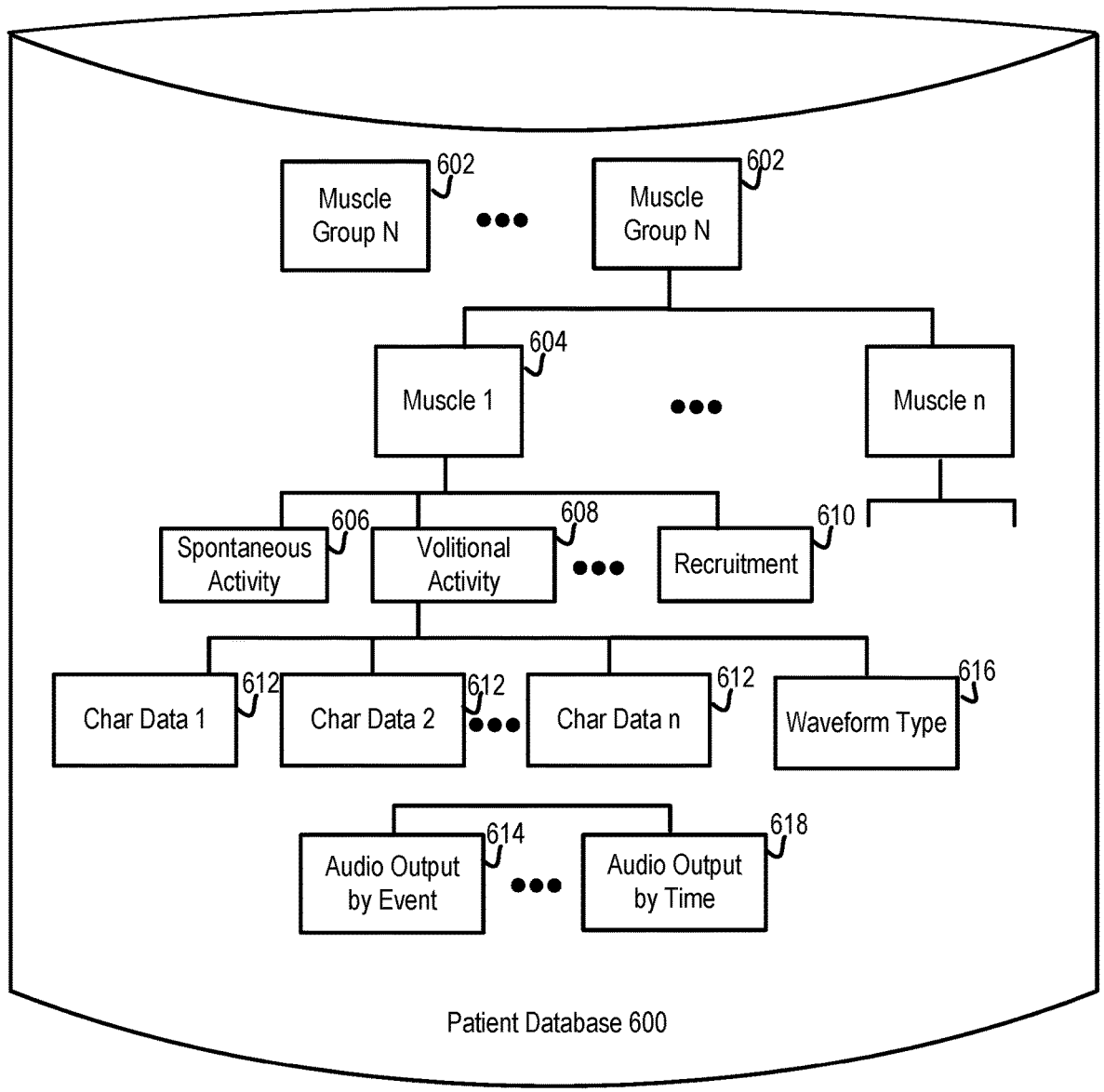
FIG. 9 illustrates a schematic block diagram of an embodiment of a patient database.

FIG. 9 illustrates a schematic block diagram of an embodiment of a patient database 600. The patient database 600 includes EMG testing results for a plurality of patients. For a particular patient, the patient database 600 includes a list of tested muscle groups 602 and one or more tested muscles 604 in each tested muscle group 602. For a tested muscle, the type of condition 608 of the EMG testing is stored, such as spontaneous activity, volitional activity and recruitment. For each type of condition, the one or more detected waveform types 616 are stored as well as characteristic data 612, such as MUP amplitude and duration and other characteristics as shown in Table 1. The audio input 614 is also stored so that it may be retrieved in whole or in part, e.g. audio input by event 614 or audio input by time 618.

For example, the EMG processing application 154 provides a graphical user interface to retrieve the audio 140 and/or list events with the time of occurrence from EMG testing of a patient. Time based events may also be replayed, such as recorded sound and waveform types. For example, the sound and the waveform of a fibrillation potential during testing of a muscle may be retrieved. The time of occurrence of the event is stored and may be retrieved during the playback review. The number of occurrences can be determined and stored as one of the characteristics 612. In another embodiment, a duration of the audio output 140, such as between a time 1 and a time 2 may be retrieved of the EMG testing. As such, recording can be displayed continuously with recognized time based events synchronized with the sound recording in step 217. Alternatively, a list of time based events or only the sound recording can be reviewed separately. In another embodiment the recording can be continuous (in default settings without the need to select individual muscles) again, recording can be displayed continuously with recognized events synchronized with the waveform and/or sound recording. Alternatively, a list of time based events or only the sound recording or only the waveform recording can be reviewed separately. In either case, the entire recording of the audio 140 may be scrolled back and forth. At the end of the exam, the entire file can be saved within the device memory 160 or memory 136.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "operably coupled to", "coupled to", and/or "coupling" includes direct coupling between items and/or indirect coupling between items via an intervening item (e.g., an item includes, but is not limited to, a component, an element, a circuit, and/or a module). As may further be used herein, inferred coupling (i.e., where one element is coupled to another element by inference) includes direct and indirect coupling between two items in the same manner as "coupled to". As may even further be used herein, the term "operable to" or "operably coupled to" indicates that an item includes one or more of functions, components, power connections, input(s), output(s), etc., to perform, when activated, one or more its corresponding functions and may further include direct or inferred coupling to one or more other items. As may still further be used herein, the term "associated with", includes direct and/or indirect association or origination or coupling of separate items and/or one item being embedded within another item.

The term "module" is used in the description of the various embodiments of the disclosure. A "module" indicates a device that includes one or more hardware components, such as a single processing device or a plurality of processing devices. A module may include a memory and software stored on the memory for performing one or more functions as may be described herein. Note that, the hardware components of a module may operate independently and/or in conjunction with software and/or firmware. As used herein, a module may contain one or more submodules, each of which may be one or more modules. As may also be used herein, a module may include one or more additional components.

The description and figures includes functional building blocks. The boundaries and sequence of these functional building blocks may have been arbitrarily defined herein for convenience of description. Alternate boundaries and sequences can be defined so long as the specified functions and relationships are appropriately performed. Any such alternate boundaries or sequences are thus within the scope and spirit of the claims. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

The disclosure may have also been described, at least in part, in terms of one or more embodiments. An embodiment of the disclosure is used herein to illustrate the disclosure, an aspect thereof, a feature thereof, a concept thereof, and/or an example thereof. A physical embodiment of an apparatus, an article of manufacture, a machine, and/or of a process that embodies the disclosure may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While particular combinations of various functions and features of the disclosure have been expressly described herein, other combinations of these features and functions are likewise possible. The disclosure is not limited by the particular examples disclosed herein and expressly incorporates these other combinations.

The invention claimed is:

1. A device, comprising:
   a display;
   an interface configured to receive an output signal of a needle electromyography (EMG) device, wherein the output signal represents one or more waveforms of electrical activity of at least one muscle;
   at least one processing device and at least one memory, wherein the at least one memory stores instructions that, when executed by the at least one processing device, causes the device to:
      determine at least one type of waveform in the output signal of the EMG device, wherein the at least one type of waveform includes one of: insertional activity waveform, spontaneous activity waveform, volitional activity waveform or recruitment waveform;
      display an identification of the determined at least one type of waveform on the display.

2. The device of claim 1, wherein the device is configured to determine the at least one type of waveform in the output signal of the EMG device by:
   identifying at least one output pattern of a plurality of output patterns in the output signal of the EMG device; and
   accessing a waveform database that associates the identified at least one output pattern with the at least one type of waveform of electrical activity of muscle fibers.

3. The device of claim 1, wherein the processing device is further configured to:
   quantify a number of motor units generating the output signal; and
   determine a count of repetitions for one or more of the motor units during a portion of the output signal.

4. The device of claim 1, wherein the processing device is configured to:
store the output signal and the identification of the determined at least one type of waveform in a patient database in the memory.

5. The device of claim 1, wherein the EMG device comprises a first stimulating electrode or needle for activating the at least one muscle fiber of the at least one muscle and a second electrode or needle for detecting the electrical activity of the at least one muscle fiber of the at least one muscle, wherein the detected electrical activity is used to generate the output signal.

6. The device of claim 1, wherein the processing device is configured to:
determine whether a sufficient number of events of insertional activity has been detected for the at least one muscle; and
indicate when the sufficient number of events of insertional activity has been detected for the at least one muscle.

7. The device of claim 1, wherein the processing device is configured to:
display a plurality of muscles in a muscle group, wherein the plurality of muscles includes the at least one muscle; and
indicate whether adequate sampling of electrical activity has been detected for each of the plurality of muscles in the muscle group.

8. The device of claim 7, wherein the adequate sampling of electrical activity includes a predetermined number of events of insertional activity.

9. The device of claim 7, wherein the processing device is configured to:
for each of the plurality of muscles in the muscle group, store the output signal, an identification of one or more events during the output signal, and a time during the output signal for each identification of the one or more events during the output signal.

\* \* \* \* \*